US00PP29693P2

(12) United States Plant Patent
Tuinier

(10) Patent No.: US PP29,693 P2
(45) Date of Patent: Sep. 18, 2018

(54) ***HAWORTHIA* PLANT NAMED "SI HAW 7026"**

(50) Latin Name: *Haworthia maxima*
Varietal Denomination: SI HAW 7026

(71) Applicant: Wander Durk Tuinier, Krimpen aan den IJssel (NL)

(72) Inventor: Wander Durk Tuinier, Krimpen aan den IJssel (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 15/530,822

(22) Filed: Mar. 3, 2017

(51) Int. Cl.
*A01H 5/12* (2018.01)

(52) U.S. Cl.
USPC ..... Plt./373

(58) Field of Classification Search
USPC ..... Plt./373
See application file for complete search history.

(56) References Cited

PUBLICATIONS

PLUTO Plant Variety Database Jan. 20, 2018. p. 1.*

* cited by examiner

*Primary Examiner* — Annette H Para
(74) *Attorney, Agent, or Firm* — C. A. Whealy

(57) ABSTRACT

A new and distinct cultivar of *Haworthia* plant named 'SI HAW 7026', characterized by its upright rosette growth habit; dark green-colored leaves with relatively large and orbicular white-colored tubercles; and excellent interiorscape performance.

2 Drawing Sheets

Botanical designation: *Haworthia maxima.*
Cultivar denomination: 'SI HAW 7026'.

BACKGROUND OF THE INVENTION

The present invention relates to a new and distinct cultivar of *Haworthia* plant, botanically known as *Haworthia maxima* and hereinafter referred to by the name 'SI HAW 7026'.

The new *Haworthia* plant is a product of a planned breeding program conducted by the Inventor in Krimpen aan den IJssel, The Netherlands. The objective of the breeding program was to develop new and distinct *Haworthia* plants with good interiorscape performance.

The new *Haworthia* plant originated from a cross-pollination made by the Inventor in 2008 of an unidentified selection of *Haworthia maxima*, not patented, as the female, or seed, parent with *Haworthia maxima* 'Donut', not patented, as the male, or pollen, parent. The new *Haworthia* plant was discovered and selected by the Inventor as a single plant within the progeny of the stated cross-pollination in a controlled greenhouse environment in Krimpen aan den IJssel, The Netherlands.

Asexual reproduction of the new *Haworthia* plant by leaf cuttings in a controlled greenhouse environment in Krimpen aan den IJssel, The Netherlands since May, 2010 has shown that the unique features of this new *Haworthia* plant are stable and reproduced true to type in successive generations.

SUMMARY OF THE INVENTION

Plants of the new *Haworthia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SI HAW 7026'. These characteristics in combination distinguish 'SI HAW 7026' as a new and distinct *Haworthia* plant:

1. Upright rosette growth habit.
2. Dark green-colored leaves with relatively large and orbicular white-colored tubercles.
3. Excellent interiorscape performance.

Plants of the new *Haworthia* differ primarily from plants of the female parent selection in leaf tubercles as leaves of plants of the female parent selection have off white-colored tubercles that are smaller and not as long as tubercles of leaves of the new *Haworthia.*

Plants of the new *Haworthia* differ primarily from plants of the male parent, 'Donut', in leaf tubercles as leaves of plants of 'Donut' have donut (or ring)-shaped tubercles.

Plants of the new *Haworthia* can be compared to plants of *Haworthia fasciata* 'Big Band', not patented. Plants of the new *Haworthia* and 'Big Band' differ primarily in the following characteristics:

1. Plants of the new *Haworthia* are smaller than plants of 'Big Band'.
2. Plants of the new *Haworthia* have thinner leaves than plants of 'Big Band'.
3. Plants of the new *Haworthia* and 'Big Band' differ in leaf color as leaves of plants of 'Big Band' are lighter green in color than leaves of plants of the new *Haworthia.*

Plants of the new *Haworthia* can also be compared to plants of *Haworthia fasciata* 'New York', disclosed in U.S. Plant Pat. No. 24,400. Plants of the new *Haworthia* and 'New York' differ primarily in the following characteristics:

1. Plants of the new *Haworthia* have shorter and thicker leaves than plants of 'New York'.
2. Plants of the new *Haworthia* and 'New York' differ in leaf tubercle pattern as plants of 'New York' have leaf tubercles that form stripe-like patterns.

BRIEF DESCRIPTION OF THE PHOTOGRAPHS

The accompanying colored photographs illustrate the overall appearance of the new *Haworthia* plant showing the colors as true as it is reasonably possible to obtain in colored reproductions of this type. Colors in the photographs may differ slightly from the color values cited in the detailed botanical description which accurately describe the colors of the new *Haworthia* plant.

The photograph on the first sheet comprises a side perspective view of a typical plant of 'SI HAW 7026' grown in a container.

The photograph on the second sheet is a top perspective view of a typical plant of 'SI HAW 7026' grown in a container.

DETAILED BOTANICAL DESCRIPTION

The aforementioned photographs and following observations, measurements and values describe plants grown during the autumn in 5.5-cm containers in a glass-covered greenhouse in Krimpen aan den IJssel, The Netherlands and under cultural practices typical of commercial *Haworthia* production. During the production of the plants, day temperatures ranged from 18° to 25° C. and night temperatures ranged from 15° to 18° C. Plants were ten months old when the photographs and description were taken. In the following description, color references are made to The Royal Horticultural Society Colour Chart, 2015 Edition, except where general terms of ordinary dictionary significance are used.

Botanical classification: *Haworthia maxima* 'SI HAW 7026'.

Parentage:

*Female, or seed, parent*.—Unidentified selection of *Haworthia maxima*, not patented.

*Male, or pollen, parent*.—*Haworthia maxima* 'Donut', not patented.

Propagation:

*Type*.—By leaf cuttings and also by meristem culture.

*Time to initiate roots, summer*.—About two weeks at temperatures about 18° C.

*Time to initiate roots, winter*.—About three weeks at temperatures about 18° C.

*Time to produce a rooted young plant, summer*.—About four weeks at temperatures about 18° C.

*Time to produce a rooted young plant, winter*.—About six weeks at temperatures about 18° C.

*Root description*.—Thick, fleshy; typically white in color, actual color of the roots is dependent on substrate composition, water quality, fertilizer type and formulation.

*Rooting habit*.—Moderately freely branching; medium density.

Plant description:

*Plant form and growth habit*.—Herbaceous perennial plant; basal rosette plant form with upright leaves; dark green-colored leaves with relatively large and orbicular white-colored tubercles; low vigor and growth rate.

*Plant height*.—About 7 cm.

*Plant width*.—About 7.9 cm.

*Interiorscape performance*.—Plants of the new *Haworthia* have excellent interiorscape performance and have been observed to typically survive about two to four years in the interiorscape.

Leaf description:

*Arrangement and quantity*.—Leaves arranged in a basal rosette, simple, generally symmetrical and long-persisting; leaves sessile; about 22 leaves per rosette.

*Leaf length*.—About 5.2 cm.

*Leaf width*.—About 2.1 cm.

*Leaf thickness*.—About 9 mm.

*Tubercle height, upper and lower surfaces*.—About 1.5 mm.

*Tubercle diameter, upper and lower surfaces*.—About 2 mm.

*Leaf shape*.—Narrowly deltoid to narrowly ovate.

*Leaf apex*.—Narrowly acute with a caudate tip.

*Leaf base*.—Broadly cuneate.

*Leaf margin*.—Entire; pustulate.

*Leaf aspect*.—Mostly flat and very slightly curved upwardly.

*Leaf texture, upper and lower surfaces*.—Glabrous; succulent; moderately pustulate.

*Leaf luster, upper and lower surfaces*.—Matte.

*Leaf venation pattern*.—Not visible.

*Leaf color*.—Developing leaves, upper surface: Close to 137A; fading towards the base, close to 160B to 160C; tubercles, close to N155A. Developing leaves, lower surface: Close to 137A; fading towards the base, close to 160B; tubercles, close to N155A. Fully expanded leaves, upper surface: Close to NN137A; fading towards the base, close to 147B and NN155B; tubercles, close to 155C. Fully expanded leaves, lower surface: Close to NN137A; fading towards the base, close to 143B and NN155B; tubercles, close to N155A.

Flower description: Flower initiation and development have not been observed to date on plants of the new *Haworthia*.

Disease & pest resistance: Plants of the new *Haworthia* have not been noted to be resistant to pathogens and pests common to *Haworthia* plants.

Temperature tolerance: Plants of the new *Haworthia* have been observed to tolerate temperatures ranging from about 5° C. to about 40° C. and to be suitable for USDA Hardiness Zones 10 to 12.

It is claimed:

1. A new and distinct *Haworthia* plant named 'SI HAW 7026' as illustrated and described.

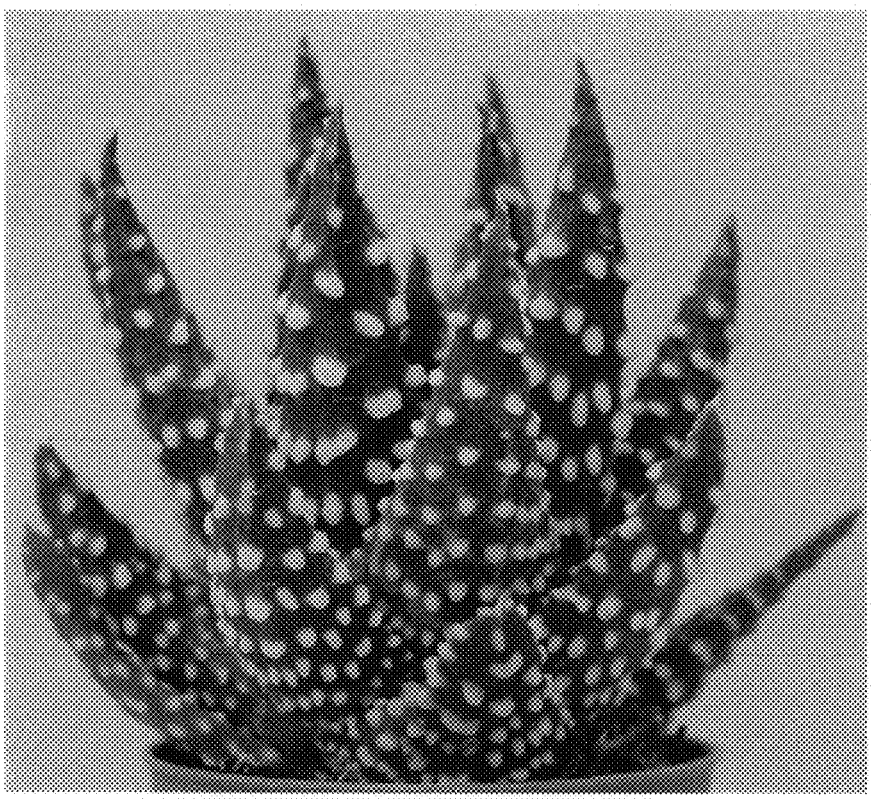

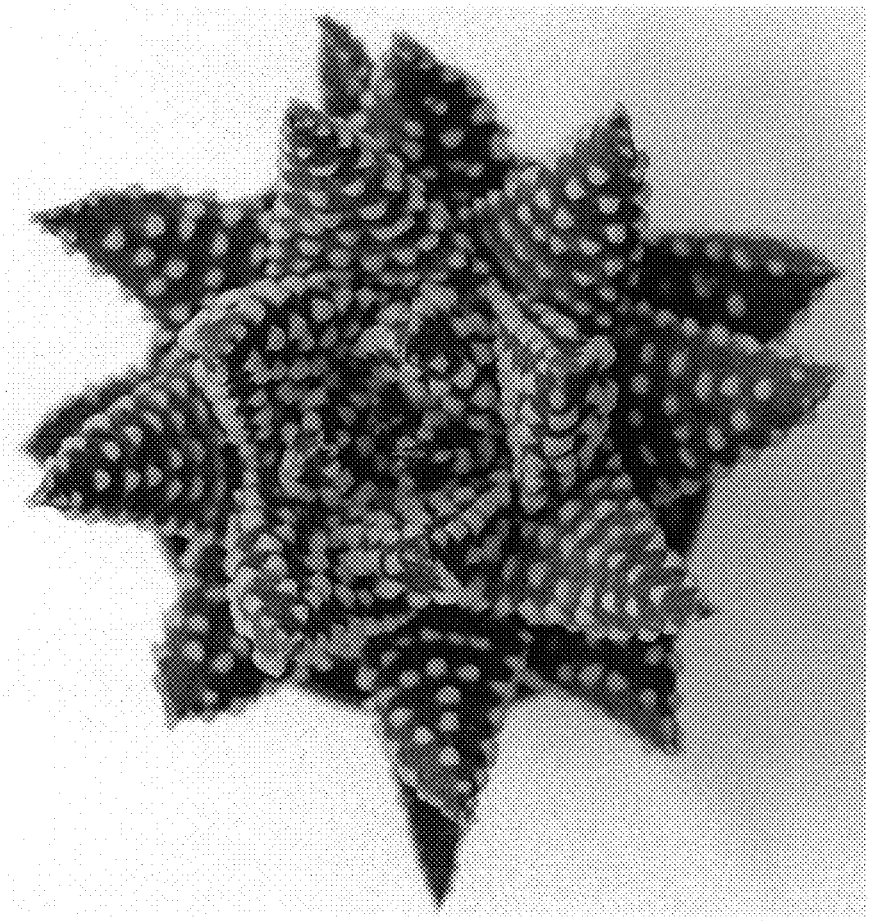

* * * * *